US009062079B2

(12) United States Patent
Kjus et al.

(10) Patent No.: US 9,062,079 B2
(45) Date of Patent: Jun. 23, 2015

(54) HYDROPHOBIC DIACRYLAMIDE COMPOUND

(71) Applicants: LIFE TECHNOLOGIES CORPORATION, Carlsbad, CA (US); LIFE TECHNOLOGIES AS, Oslo (NO)

(72) Inventors: Nini Kjus, Oslo (NO); Geir Fonnum, Fjellhamar (NO); Bruce Branchaud, Eugene, OR (US); Lai-Qiang Ying, Eugene, OR (US); Steven Menchen, Fremont, CA (US); Dmitriy Gremyachinskiy, Eugene, OR (US); Hee Chol Kang, Eugene, OR (US)

(73) Assignee: Life Technologies Corporation, Carlsbad, CA (US)

( * ) Notice: Subject to any disclaimer, the term of this patent is extended or adjusted under 35 U.S.C. 154(b) by 256 days.

(21) Appl. No.: 13/762,489

(22) Filed: Feb. 8, 2013

(65) Prior Publication Data
US 2013/0211119 A1 Aug. 15, 2013

Related U.S. Application Data

(60) Provisional application No. 61/597,060, filed on Feb. 9, 2012.

(51) Int. Cl.
C07F 7/18 (2006.01)
C07F 7/10 (2006.01)
C08F 222/38 (2006.01)
C08F 220/58 (2006.01)
C08F 236/20 (2006.01)
C08K 3/20 (2006.01)

(52) U.S. Cl.
CPC .............. C07F 7/10 (2013.01); C07F 7/1804 (2013.01); C07F 7/1852 (2013.01); C08F 222/385 (2013.01); C08F 220/58 (2013.01); C08F 236/20 (2013.01); C08K 3/20 (2013.01)

(58) Field of Classification Search
CPC .................................................. C07F 7/11804
USPC ............................................................ 556/419
See application file for complete search history.

(56) References Cited

U.S. PATENT DOCUMENTS

| 4,451,613 | A | 5/1984 | Rousseau et al. |
| 4,507,382 | A | 3/1985 | Rousseau et al. |
| 4,507,497 | A | 3/1985 | Reilly, Jr. et al. |
| 4,511,646 | A | 4/1985 | Forenkamm et al. |
| 5,455,143 | A | 10/1995 | Ali |
| 5,677,373 | A | 10/1997 | Berge et al. |
| 7,217,762 | B1 | 5/2007 | Jorgedal et al. |
| 2004/0215011 | A1 | 10/2004 | Deggerdal et al. |
| 2005/0014001 | A1 | 1/2005 | Fonnum et al. |
| 2006/0131542 | A1 | 6/2006 | Weng et al. |
| 2007/0231354 | A1 | 10/2007 | Sogabe et al. |
| 2007/0249797 | A1 | 10/2007 | Golova et al. |
| 2007/0299249 | A1 | 12/2007 | Songe |
| 2008/0139399 | A1 | 6/2008 | Fonnum et al. |
| 2008/0300383 | A1 | 12/2008 | Verdianz et al. |
| 2009/0069554 | A1 | 3/2009 | Finne |
| 2009/0291506 | A1 | 11/2009 | Fonnum et al. |
| 2010/0207051 | A1 | 8/2010 | Fonnum et al. |

FOREIGN PATENT DOCUMENTS

| JP | 2007/217447 | 8/2007 |
| WO | 2010/125170 | 11/2010 |

OTHER PUBLICATIONS

Clericuzio et al, Eur. J. Org. Chem. 2007, 5551-5559.*
Dufour, et al., "A Study of the Hetero Diels-Alder Reaction of N-Alkyl-2-Cyano-1-Azadienes with 2-Vinylindole", Heterocycles, vol. 37, No. 3, Oct. 8, 1993, pp. 1455-1458.
Schumann, et al., "Synthesis and Characterization of Water-Soluble Tin-Based Metallodendrimers", Organometallics. vol. 22, 2003, pp. 2034-2041.
Skinner, et al., "Effect of Organic Compounds on Reproductive Processes. VI. Alkylating Agents Derived from Various Diamines", Journal of Medicinal Chemistry, vol. 10, No. 5, Sep. 1967, pp. 949-950.
Klee, J. et al., "N-alkyl-N-(phosphonoethyl) substituted (meth)acrylamides—new adhesive monomers for self-etching self-priming one part dental adhesive" Beilstein Journal of Organic Chemistry, vol. 5, No. 72, 2009, pp. 1-9.
PCT/US2013/025259 International Search Report and Written Opinion dated Apr. 17, 2013.
Bierstedt, Anja et al., "A Symmetry-Based Approach to the Heterobicyclic core of the zaragozic acids-model studies in the C2-Symmetric series", Tetrahedron Letters vol. 44, 2003, pp. 7867-7870.
Clericuzio, Marco, "Non-Phenolic Dicinnamamides from Pholiota Spumosa: Isolation, Synthesis and Antitumour Activity", Eur. J. Org. Chem, 2007, pp. 5551-5559.
Yamaoka, Tsuguo et al., "A Study of Novel Heat-Resistant Polymers: Preparation of Photosensitive Fluorinated Polybenzoxazole Precursors and Physical Properties of Polybenzoxazole Derived from the Precursors", Journal of Polymer Science: Part A: Polymer Chenistry, vol. 28, John Wiley & Sons, Inc., 1990, pp. 2517-2532.

* cited by examiner

Primary Examiner — Sudhakar Katakam
Assistant Examiner — Kofi Adzamli

(57) ABSTRACT

A silyl protected diacrylamide compound is described. A method of forming such a compound includes mixing a silylation reagent with a hydroxylated diamine compound under first reactive conditions to form a product in a first solution, separating the product from the first solution, and mixing the product with acryloyl chloride under second reactive conditions in a second solution to form a silyl protected diacrylamide compound.

20 Claims, No Drawings

HYDROPHOBIC DIACRYLAMIDE COMPOUND

CROSS-REFERENCE TO RELATED APPLICATION(S)

This application claims benefit of U.S. Provisional Application No. 61/597,060, filed Feb. 9, 2012, which is incorporated herein by reference in its entirety.

FIELD OF THE DISCLOSURE

This disclosure, in general, relates to protected diacrylamide compounds and methods for making same.

BACKGROUND

Multi-functional compounds have a variety of uses. For example, multi-functional compounds find use in synthesis reactions to form symmetric compounds or to form cyclic compounds. In another example, multi-functional compounds find use in polymerization reactions, for example, as crosslinkers. Such crosslinkers can influence the physical properties of a polymer, such as glass transition temperature, or can influence mechanical properties, such as flexibility or shear resistance.

SUMMARY

In a first aspect, a compound has formula I below or an analog thereof, wherein R1 and R2 are independently selected from alkyl, heteroalkyl, cycloalkyl, hydroxyalkyl, acyl, aryl, ether derivatives thereof, or a combination thereof, and R3, R4, R5, R6, and R7 are independently selected from alkyl, heteroalkyl, cycloalkyl, hydroxyalkyl, acyl, oxycarbonyl, aryl, ether derivatives thereof, a silyl, or a combination thereof.

In a second aspect, a compound has the formula II below or an analog thereof, wherein R1 or R2 are independently selected from alkyl, heteroalkyl, cycloalkyl, hydroxyalkyl, acyl, aryl, ether derivatives thereof, or a combination thereof, and R3, R4, or R5 are independently selected from hydrogen, alkyl, heteroalkyl, cycloalkyl, hydroxyalkyl, acyl, aryl, ether derivatives thereof, or a combination thereof.

In a third aspect, a compound has the formula III below or an analog thereof, R1, R2, or R3 are independently selected from alkyl, heteroalkyl, cycloalkyl, hydroxyalkyl, acyl, aryl, ether derivatives thereof, or a combination thereof.

In a fourth aspect, a compound has the formula XII below or an analog thereof, wherein R4, R5, or R6 are independently selected from alkyl, heteroalkyl, cycloalkyl, hydroxyalkyl, acyl, aryl, ether derivatives thereof, or a combination thereof, and R1, R2, R3, R7, R8, or R9 are independently selected from alkyl, heteroalkyl, cycloalkyl, hydroxyalkyl, acyl, aryl, ether derivatives thereof, or a combination thereof.

In a fifth aspect, a compound has the formula XIII below or an analog thereof, wherein R4 or R5 are independently selected from alkyl, heteroalkyl, cycloalkyl, hydroxyalkyl, acyl, aryl, ether derivatives thereof, or a combination thereof, and R1, R2, R3, R6, R7, or R8 are independently selected from alkyl, heteroalkyl, cycloalkyl, hydroxyalkyl, acyl, aryl, ether derivatives thereof, or a combination thereof.

In a sixth aspect, a compound has the formula VII below or an analog thereof, wherein R1 or R2 are independently selected from alkyl, heteroalkyl, cycloalkyl, hydroxyalkyl, acyl, aryl, ether derivatives thereof, or a combination thereof or represent a direct bond between a nitrogen and a hydroxylated carbon, and R3, R4, R5, R6, R7, R8, R9, or R10 are independently selected from hydrogen, alkyl, heteroalkyl, cycloalkyl, hydroxyalkyl, acyl, oxycarbonyl, aryl, ether derivatives thereof, silyl, or a combination thereof.

In a seventh aspect, a method of forming a compound includes mixing an activated acrylate and a hydroxylated diamine compound to form a hydroxylated diacrylamide compound, separating the hydroxylated diacrylamide compound, and mixing a silylation reagent with the hydroxylated diacrylamide compound under reactive conditions to form a silyl protected diacrylamide compound.

In an eighth aspect, a method of forming a compound includes mixing a silylation reagent with a hydroxylated diacrylamide under reactive conditions to form silyl protected diacrylamide in a solution and separating the silyl protected diacrylamide from the solution.

In a ninth aspect, a method of forming a compound includes mixing a silylation reagent with a hydroxylated diamine compound under first reactive conditions to form a product in a first solution, separating the product from the first solution, and mixing the product with an activated acrylate under second reactive conditions in a second solution to form a silyl protected diacrylamide compound.

In a tenth aspect, a method of forming a polymer includes mixing in a hydrophobic phase, a monomer and a compound having a formula below, the monomer and the compound polymerizing to form the polymer.

In an eleventh aspect, a composition includes a non-aqueous solution including a diacrylamide crosslinker and a free radical polymerizable monomer.

DETAILED DESCRIPTION

In an exemplary embodiment, a multifunctional compound includes at least two acrylamide functional groups or derivatives thereof, such as at least two acrylamide terminal functional groups or methacrylamide terminal functional groups. A derivative of an acrylamide includes an acrylamide analog, such as methacrylamide, ethacrylamide, or a combination thereof. In particular, the multifunctional compound can be a diacrylamide. In another example, the multifunctional compound can be a diacrylamide analog, such as a di-methacrylamide. An exemplary diacrylamide or analog thereof includes one or more hydrophilic functional groups other than the acrylamide functional groups. In particular, the hydrophilic functional group can include hydroxyl, amine, or a combination thereof. In a particular embodiment, the hydrophilic functional group is hydroxyl. The hydrophilic functional group is protected with a protection group, such as a silyl groups and derivatives thereof, in which hydrogens are replaced with a hydrocarbon, halogen (e.g., Cl), trifluoromethanesulfonate, or a further silyl group. Such multifunctional compounds find particular use as precursors in synthesis reactions or function as crosslinkers in polymerization reactions.

In a further embodiment, a multi- or diacrylamide compound can be formed from a multi- or diamine compound that includes a hydroxyl group. For example, the hydroxyl group can be protected with a silyl group, such as through reaction of the hydroxyl group with a halogenated silyl group. Following protection with silyl groups, the amine groups of the multi- or diamine can be reacted with an activated acrylate, such as acryloyl chloride or acryloyl anhydride, to form a multi- or di-acrylamide. In an alternative method, an acrylamide having one or more hydroxyl groups can be protected by reacting the hydroxyl groups with a halogenated silyl group.

In a particular example, a diacrylamide compound has the general formula:

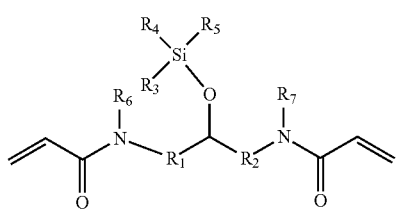

(I)

wherein R1 or R2 are independently selected from alkyl, heteroalkyl, cycloalkyl, hydroxyalkyl, acyl, aryl, ether derivatives thereof, or a combination thereof, and R3, R4, R5, R6, or R7 are independently selected from hydrogen, alkyl, heteroalkyl, cycloalkyl, hydroxyalkyl, acyl, aryl, ether derivatives thereof, or a combination thereof. While the vinyl groups are illustrated as including hydrogen, one or more hydrogens on the vinyl group can be placed with a halogen, such as chlorine, fluorine, or combination thereof. Alternatively, the compound can be an analog of the above compound.

In an example, R1 or R2 of formula I independently can be a C1-C6 alkyl, such as a methyl or ethyl group. In another example, R1 or R2 independently can be hydroxyalkyl.

In another example, R6 or R7 independently can be selected from selected from alkyl, heteroalkyl, cycloalkyl, hydroxyalkyl, acyl, oxycarbonyl, aryl, ether derivatives thereof, silyl, or a combination thereof. For example, R6 or R7 can be hydrogen. In a further example, R6 or R7 can be a C1-C6 alkyl, such as a methyl, ethyl, propyl, or butyl, or ether derivatives thereof. In particular, the alkyl can be linear or branched. For example, propyl includes n-propyl or iso-propyl, and butyl includes n-butyl, iso-butyl, sec-butyl, or tert-butyl. In an additional example, R6 or R7 independently can be aryl, such as a phenyl, tolyl, xylyl, or poly-aryl, such as naphthyl, or ether derivatives thereof.

In a further example, R3, R4, or R5 independently can be selected from alkyl, heteroalkyl, cycloalkyl, hydroxyalkyl, acyl, aryl, ether derivatives thereof, or a combination thereof. For example, R3, R4, or R5 can be hydrogen. In a further example, R3, R4, or R5 can be a C1-C6 alkyl, such as a methyl, ethyl, propyl or butyl, or ether derivatives thereof. For example, R3, R4, or R5 can be an ethyl, propyl or butyl, or ether derivatives thereof. In particular, the alkyl can be linear or branched. In example, at least one of R3, R4, or R5 can be a branched alkyl. For example, propyl includes n-propyl or iso-propyl, and butyl includes n-butyl, iso-butyl, sec-butyl, or tert-butyl. In an additional example, R3, R4, or R5 independently can be an aryl, such as a phenyl, tolyl, xylyl, or poly-aryl, such as naphthyl, or ether derivatives thereof.

In a particular example of formula I, R6 and R7 are hydrogen, providing a diacrylamide of the formula:

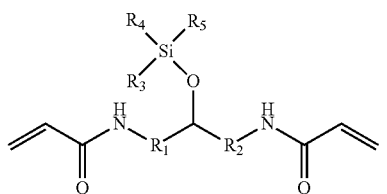

(II)

wherein R1 or R2 are independently selected from alkyl, heteroalkyl, cycloalkyl, hydroxyalkyl, acyl, aryl, ether derivatives thereof, or a combination thereof, and R3, R4, or R5 are independently selected from alkyl, heteroalkyl, cycloalkyl, hydroxyalkyl, acyl, aryl, ether derivatives thereof, or a combination thereof. While the vinyl groups are illustrated as including hydrogen, one or more hydrogens on the vinyl group can be placed with a halogen, such as chlorine, fluorine, or combination thereof. Alternatively, the compound can be an analog of the above compound.

In an example, R1 or R2 of formula II independently can be a C1-C6 alkyl, such as a methyl or ethyl group. In another example, R1 or R2 independently can be hydroxyalkyl.

In a further example, R3, R4, or R5 independently can be selected from alkyl, heteroalkyl, cycloalkyl, hydroxyalkyl, acyl, aryl, ether derivatives thereof, or a combination thereof. In a further example, R3, R4, or R5 can be a C1-C6 alkyl, such as a methyl, ethyl, propyl or butyl, or ether derivatives thereof. For example, R3, R4, or R5 can be an ethyl, propyl or butyl, or ether derivatives thereof. In particular, the alkyl can be linear or branched. In example, at least one of R3, R4, or R5 can be a branched alkyl. For example, propyl includes n-propyl or iso-propyl, and butyl includes n-butyl, iso-butyl, sec-butyl, or tert-butyl. In an additional example, R3, R4, or R5 independently can be an aryl, such as a phenyl, tolyl, xylyl, or poly-aryl, such as naphthyl, or ether derivatives thereof.

In an example, R1 and R2 of formula II are methyl, providing a diacrylamide of the following formula:

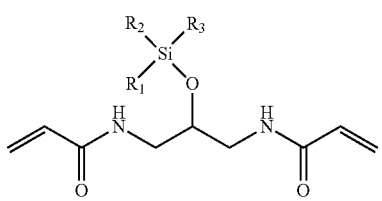

(III)

wherein R1, R2, or R3 are independently selected from alkyl, heteroalkyl, cycloalkyl, hydroxyalkyl, acyl, aryl, ether derivatives thereof, or a combination thereof. While the vinyl groups are illustrated as including hydrogen, one or more hydrogens on the vinyl group can be placed with a halogen, such as chlorine, fluorine, or combination thereof. Alternatively, the compound can be an analog of the above compound, such as a methacrylamide analog. For example, R1, R2, or R3 can be a C1-C6 alkyl, such as a methyl, ethyl, propyl or butyl, or ether derivatives thereof. For example, R1, R2, or R3 can be an ethyl, propyl or butyl, or ether derivatives thereof. In particular, the alkyl can be linear or branched. In example, at least one of R3, R4, or R5 can be a branched alkyl. For example, propyl includes n-propyl or iso-propyl, and butyl includes n-butyl, iso-butyl, sec-butyl, or tert-butyl. In an additional example, R1, R2, or R3 independently can be an aryl, such as a phenyl, tolyl, xylyl, or poly-aryl, such as naphthyl, or ether derivatives thereof.

In a particular example of formula III, R1, R2, and R3 are ethyl, providing a diacrylamide of the following formula, which has a log(p) value of 1.84.

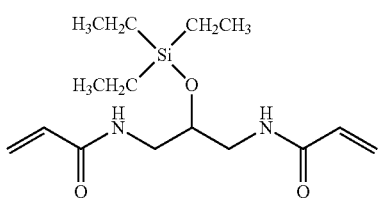

(IV)

In another example of formula III, R1 and R3 are methyl and R2 is tert-butyl, providing a diacrylamide of the following formula, which has a log(p) value of 1.8.

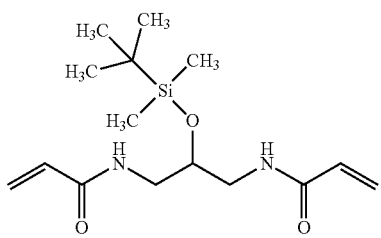

(V)

In an additional example of formula III, R1 and R2 are methyl and R3 is phenyl, providing a diacrylamide of the following formula, which has a log(p) value of 1.77.

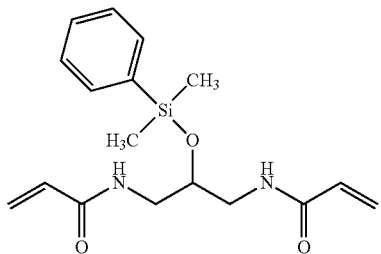

(V)

In a further example of a multi-functional acrylamide compound, a diacrylamide compound has the following formula:

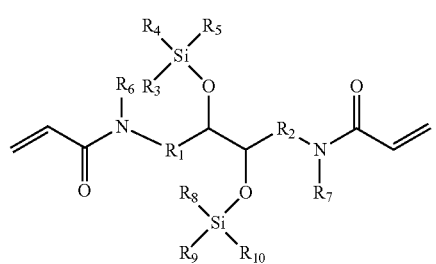

(VII)

wherein R1 or R2 are independently selected from alkyl, heteroalkyl, cycloalkyl, hydroxyalkyl, acyl, aryl, ether derivatives thereof, or a combination thereof or represent a direct bond between a nitrogen and a hydroxylated carbon, and R3, R4, R5, R6, R7, R8, R9, or R10 are independently selected from alkyl, heteroalkyl, cycloalkyl, hydroxyalkyl, acyl, oxycarbonyl, aryl, ether derivatives thereof, silyl, or a combination thereof. While the vinyl groups are illustrated as including hydrogen, one or more hydrogens on the vinyl group can be placed with a halogen, such as chlorine, fluorine, or combination thereof. Alternatively, the compound can be an analog of the above compound. In a further example, the compound can be monosilylated where one of the silyl groups of the above formula is replaced with a hydroxide or alkoxy group.

In an example, R1 or R2 of formula VII independently can be a C1-C6 alkyl, such as a methyl or ethyl group. In another example, R1 or R2 independently can be hydroxyalkyl. In a particular example, R1 and R2 represent a direct bond between a nitrogen and a hydroxylated carbon.

In another example, R6 or R7 independently can be selected from selected from hydrogen, alkyl, heteroalkyl, cycloalkyl, hydroxyalkyl, acyl, oxycarbonyl, aryl, ether derivatives thereof, silyl, or a combination thereof. For example, R6 or R7 can be hydrogen. In a further example, R6 or R7 can be a C1-C6 alkyl, such as a methyl, ethyl, propyl, or butyl, or ether derivatives thereof. In particular, the alkyl can be linear or branched. For example, propyl includes n-propyl or iso-propyl, and butyl includes n-butyl, iso-butyl, sec-butyl, or tert-butyl. In an additional example, R6 or R7 independently can be aryl, such as a phenyl, tolyl, xylyl, or poly-aryl, such as naphthyl, or ether derivatives thereof.

In a further example, R3, R4, R5, R8, R9, or R10 independently can be selected from alkyl, heteroalkyl, cycloalkyl, hydroxyalkyl, acyl, aryl, ether derivatives thereof, or a combination thereof. In a further example, R3, R4, R5, R8, R9, or R10 can be a C1-C6 alkyl, such as a methyl, ethyl, propyl or butyl, or ether derivatives thereof. For example, R3, R4, or R5 can be an ethyl, propyl or butyl, or ether derivatives thereof or R8, R9, or R10 can be an ethyl, propyl or butyl, or ether derivatives thereof. In particular, the alkyl can be linear or branched. In example, at least one of R3, R4, or R5 can be a branched alkyl or at least one of R8, R9, or R10 can be a branched alkyl. For example, propyl includes n-propyl or iso-propyl, and butyl includes n-butyl, iso-butyl, sec-butyl, or tert-butyl. In an additional example, R3, R4, R5, R8, R9, or R10 independently can be an aryl, such as a phenyl, tolyl, xylyl, or poly-aryl, such as naphthyl, or ether derivatives thereof.

In an example of formula VII, R1 and R2 represent a direct bond between nitrogen and a hydroxylated carbon and R6 and R7 are hydrogen, providing a diacrylamide compound of the formula:

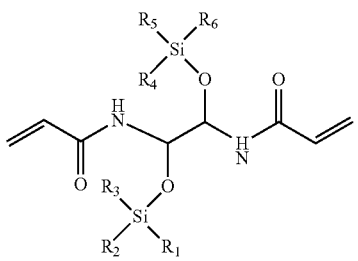

(VIII)

wherein R1, R2, R3, R4, R5, or R6 are independently selected from hydrogen, alkyl, heteroalkyl, cycloalkyl, hydroxyalkyl, acyl, aryl, ether derivatives thereof, or a combination thereof. While the vinyl groups are illustrated as including one or more hydrogens on the vinyl group can be placed with a halogen, such as chlorine, fluorine, or combination thereof. In a further example, R1, R2, R3, R4, R5, or R6 can be a C1-C6 alkyl, such as a methyl, ethyl, propyl or butyl, or ether derivatives thereof. For example, R1, R2, or R3 can be an ethyl, propyl or butyl, or ether derivatives thereof or R3, R4, or R5 can be an ethyl, propyl or butyl, or ether derivatives thereof. In particular, the alkyl can be linear or branched. In example, at least one of R1, R2, or R3 can be a branched alkyl or at least one of R3, R4, or R5 can be a branched alkyl. For example, propyl includes n-propyl or iso-propyl, and butyl includes n-butyl, iso-butyl, sec-butyl, or tert-butyl. In an additional example, R1, R2, R3, R4, R5, or R6 independently can be an aryl, such as a phenyl, tolyl, xylyl, or poly-aryl, such as naphthyl, or ether derivatives thereof. Alternatively, the compound can be an analog of the above compound, such as a methacrylamide or ethacrylamide analog of the above compound. In a further example, the compound can be monosilylated where one of the silyl groups of the above formula is replaced with a hydroxide or alkoxy group.

In a particular example of formula VIII, R1, R2, R3, R4, R5, and R6 are ethyl, providing a diacrylamide compound having the following formula, which has a log(p) value of 4.92.

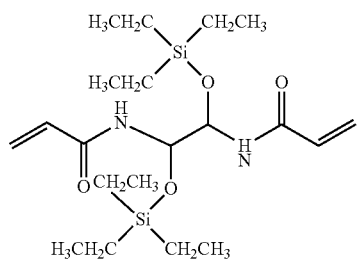

In a further example of formula VIII, R1, R3, R4, and R6 are methyl and R2 and R5 are tert-butyl, providing a diacrylamide compound of the following formula, which has a log(p) value of 4.85.

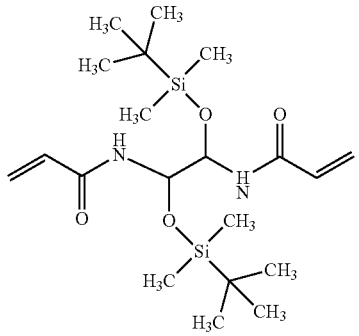

In an additional example of formula VIII, R1, R3, R4, and R6 are methyl and R2 and R5 are phenyl, providing a diacrylamide compound of the following formula, which has a log(p) value of 4.79

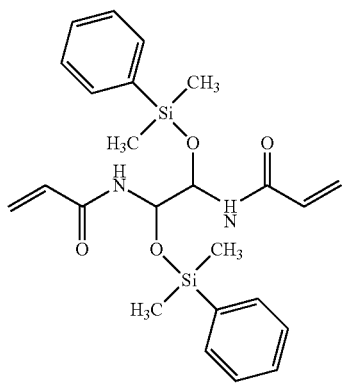

In another example of a multifunctional acrylamide compound, a diacrylamide has the formula:

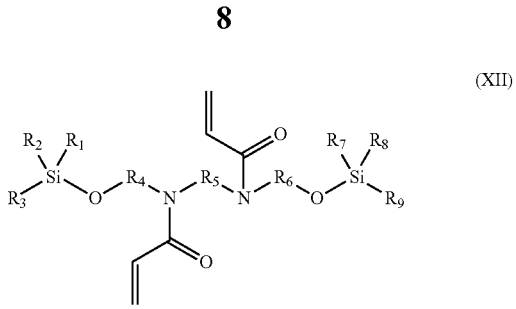

wherein R4, R5, or R6 are independently selected from alkyl, heteroalkyl, cycloalkyl, hydroxyalkyl, acyl, aryl, ether derivatives thereof, or a combination thereof, and R1, R2, R3, R7, R8, or R9 are independently selected from alkyl, heteroalkyl, cycloalkyl, hydroxyalkyl, acyl, aryl, ether derivatives thereof, or a combination thereof. While the vinyl groups are illustrated as including hydrogen, one or more hydrogens on the vinyl group can be placed with a halogen, such as chlorine, fluorine, or combination thereof. Alternatively, the compound can be an analog of the above compound, such as a methacrylamide or ethacrylamide analog of the above compound. In a further example, the compound can be monosilylated where one of the silyl groups of the above formula is replaced with a hydroxide or alkoxy group.

In an example, R5 of formula XII independently can be C1-C6 alkyl, such as a methyl or ethyl group. In an additional example, R4 or R6 of formula XII independently can be C1-C6 alkyl, such as a methyl or ethyl group. In another example, R4, R5, or R6 independently can be hydroxyalkyl.

In a further example, R1, R2, R3, R7, R8, or R9 independently can be selected from alkyl, heteroalkyl, cycloalkyl, hydroxyalkyl, acyl, aryl, ether derivatives thereof, or a combination thereof. In a further example, R1, R2, R3, R7, R8, or R9 can be a C1-C6 alkyl, such as a methyl, ethyl, propyl or butyl, or ether derivatives thereof. For example, R1, R2, or R3 can be an ethyl, propyl or butyl, or ether derivatives thereof or R7, R8, or R9 can be an ethyl, propyl or butyl, or ether derivatives thereof. In particular, the alkyl can be linear or branched. In example, at least one of R1, R2, or R3 can be a branched alkyl or at least one of R7, R8, or R9 can be a branched alkyl. For example, propyl includes n-propyl or iso-propyl, and butyl includes n-butyl, iso-butyl, sec-butyl, or tert-butyl. In an additional example, R1, R2, R3, R7, R8, or R9 independently can be an aryl, such as a phenyl, tolyl, xylyl, or poly-aryl, such as naphthyl, or ether derivatives thereof.

In a particular example of formula XII, R5 can be ethyl, providing a diacrylamide compound of the formula:

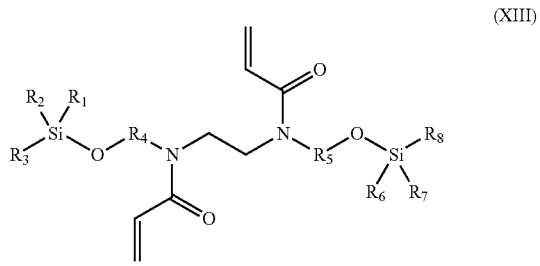

wherein R4 or R5 are independently selected from alkyl, heteroalkyl, cycloalkyl, hydroxyalkyl, acyl, aryl, ether derivatives thereof, or a combination thereof, and R1, R2, R3, R6, R7, or R8 are independently selected from alkyl, heteroalkyl, cycloalkyl, hydroxyalkyl, acyl, aryl, ether derivatives thereof, or a combination thereof. While the vinyl groups are illustrated as including hydrogen, one or more hydrogens on the vinyl group can be placed with a halogen, such as chlorine, fluorine, or combination thereof. Alternatively, the compound can be an analog of the above compound. In a further example, the compound can be monosilylated where one of the silyl groups of the above formula is replaced with a hydroxide or alkoxy group.

In an example, R4 or R5 of formula XIII independently can be C1-C6 alkyl, such as a methyl or ethyl group. In another example, R4 or R5 independently can be hydroxyalkyl.

In a further example, R1, R2, R3, R6, R7, or R8 independently can be selected from alkyl, heteroalkyl, cycloalkyl, hydroxyalkyl, acyl, aryl, ether derivatives thereof, or a combination thereof. In a further example, R1, R2, R3, R6, R7, or R8 can be a C1-C6 alkyl, such as a methyl, ethyl, propyl or butyl, or ether derivatives thereof. For example, R1, R2, or R3 can be an ethyl, propyl or butyl, or ether derivatives thereof or R6, R7, or R8 can be an ethyl, propyl or butyl, or ether derivatives thereof. In particular, the alkyl can be linear or branched. In example, at least one of R1, R2, or R3 can be a branched alkyl or at least one of R6, R7, or R8 can be a branched alkyl. For example, propyl includes n-propyl or iso-propyl, and butyl includes n-butyl, iso-butyl, sec-butyl, or tert-butyl. In an additional example, R1, R2, R3, R6, R7, or R8 independently can be an aryl, such as a phenyl, tolyl, xylyl, or poly-aryl, such as naphthyl, or ether derivatives thereof.

In a particular example of formula XIII, R4 and R5 are ethyl and R1, R2, R3, R6, R7, and R8 are ethyl, providing a diacrylamide of the following formula, which has a log(p) value of 4.51.

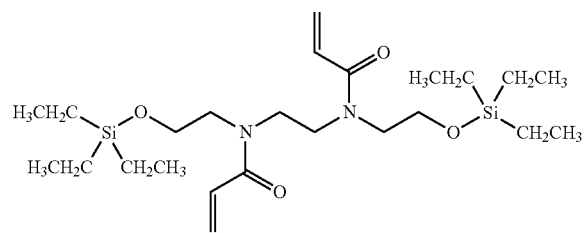

(XIV)

In another example of formula XIII, R4 and R5 are ethyl, R1, R3, R6, and R8 are methyl, and R2 and R5 are tert-butyl, providing a diacrylamide of the following formula, which has a log(p) value of 4.44.

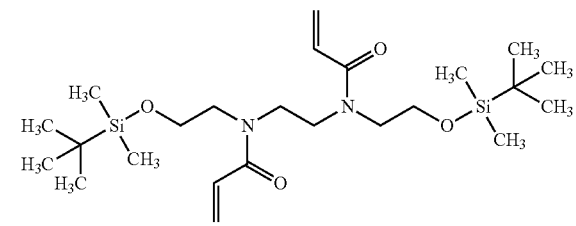

(XV)

In another example of formula XIII, R4 and R5 are ethyl, R1, R3, R6, and R8 are methyl, and R2 and R5 are phenyl, providing a diacrylamide of the following formula, which has a log(p) value of 4.38.

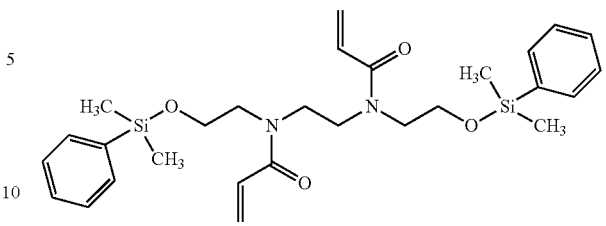

(XVI)

Alternatively, each of the above compounds I-XVI can be an analog of the illustrated compound. An exemplary analog can include a methacrylamide, an ethacrylamide analog of the above compounds, or combinations thereof. In a further example, those of the above compounds illustrated as including two silyl groups can be monosilylated wherein one of the silyl groups is replaced with a hydroxide or alkoxy group.

In an exemplary embodiment, such acrylamide compounds can find use as a crosslinker in a polymerization reaction. In particular, such protected diacrylamide crosslinkers can be utilized in polymerization reactions carried out in non-aqueous hydrophobic solvents. A protected diacrylamide can be more hydrophobic than hydrophilic. When polymerization is carried out in an emulsion or similar process, such protected diacrylamides can preferentially reside in a hydrophobic phase. For example, an oil-in-water emulsion can be formed in which the polymerization reaction takes place in the oil dispersed phase. Such hydrophobic diacrylamide crosslinkers can preferentially reside or transport to the oil phase to participate in the polymerization reaction. In another example, a hydrophobic dispersed phase in which polymerization occurs can be formed from a promoted polymeric particle, such as a polystyrene or polyacrylate particle promoted with dioctanoyl peroxide, dioctyladipate, n-butyl phthalate, dodecanol, polystyrene with molecular weight below 20 kD, or a combination thereof. Such protected diacrylamides can preferentially reside in the hydrophobic dispersed phase.

Such diacrylamide crosslinkers are typically useful in free radical initiated polymerization reactions. Exemplary free radical polymerizable monomers include acrylamide, vinyl acetate, hydroxyalkylmethacrylate, or any combination thereof. Such diacrylamide crosslinkers find use particularly in such free radical polymerization reactions carried out a hydrophobic phase or solvent.

In an example, a composition includes a diacrylamide crosslinker and a free radical polymerizable monomer in a non-aqueous solution. The composition can include the diacrylamide crosslinker in an amount relative to the free radical polymerizable monomer in a range of 0.01 wt % to 30 wt %, such as a range of 0.05 wt % to 15 wt %, a range of 0.05 wt % to 8 wt %, or even a range of 0.1 wt % to 5 wt %. In a further example, the composition can include an aqueous phase within which the non-aqueous solution is dispersed, such as in an emulsion.

After polymerization, the resulting polymer can include the silyl functional groups. The polymer can be deprotected, removing the silyl functional groups. For example, the polymer can be deprotected through acid cleaving, leaving hydroxyl groups in place of the silyl groups.

In an example, the above classes of compounds permit deprotection (e.g., removal of the silyl groups) with limited hydrolysis of the non-silyl elements of the compounds. Such a technical advantage is particularly desirable when polymerizing in a multiphase system (e.g., oil-in-water), when a hydrophilic end product is desired, when exposed hydroxyl groups are desired in the end product, or any combination thereof.

In a particular example, the estimated logarithm of the partition coefficient (n-Octanol/Water) as determined using ChemBioDraw Ultra version 13.0 using C in place of Si, herein "log(p)," of the compound is greater than 1.0 and the log(p) of a deprotected analogous compound in which the silyl groups are replaced with a hydroxyl group is not greater than 1.0. For example, the log(p) of the compound can be at least 1.2, such as at least 1.3, at least 1.5, at least 1.8, or even at least 2.0. The log(p) of the compound can be not greater than 10.0, such as not greater than 5.0. The log(p) of the analogous compound can be not greater than 0.8, such as not greater than 0.7, not greater than 0.6, not greater than 0.5, not greater than 0, or even not greater than −0.5. The log(p) of the analogous compound can be at least −10.0, such as at least −5.0.

Protected multi-acrylamide or diacrylamide compounds, or analogs, can be formed by forming an acrylamide compound or analog having unprotected hydrophilic groups, followed by protecting the hydrophilic groups. Alternatively, the protected multi-acrylamide or diacrylamide compound can be formed by protecting non-amine hydrophilic groups of a compound including multiple amine groups, followed by forming an acrylamide or analog from the amine groups.

In an example, a silylation reagent, such as silyl chloride, silyl triflate, or silazane, and a hydroxylated diamine compound are mixed in a solvent to form a silyl protected diamine compound. For example, the silyl chloride can be tert-butyldimethylsilyl chloride, trimethylsilyl chloride, triethylsilyl chloride, diphenyl methyl silyl chloride, chlorotriphenylsilane, or a combination thereof. In an example, the silyl trifluoromethanesulfonates ("triflate") include tert-butyldimethylsilyl trifluoromethanesulfonate, trimethylsilyl trifluoromethanesulfonate, triethylsilyl trifluoromethanesulfonate, or a combination thereof. An example of a silazane includes diphenylmethyl(dimethylamino)silane. An exemplary hydroxylated diamine includes alkyl-diyl bis hydroxyalkyl acrylamide, hydroxyalkyl diyl-diacrylamide, bishydroxyalkyl-diyl diacrylamide, a derivative thereof, or a combination thereof. The solvent can include a DMF solvent. In addition, the mixture can include imidazole or a derivative thereof. The reactive mixture can be stirred for at least 8 hours under an inert atmosphere. The silyl protected diamine compound is extracted and dried. For example, the silyl protected diamine compound can be extracted with diethyl ether or dichloromethane and washed with a buffered aqueous solution.

The silyl protected diamine compound can be mixed with a solution including an activated acrylate, such as acryloyl chloride or acryloyl anhydride, or an activated alkylacrylate analog, to form a protected diacrylamide compound or analog thereof. The solution can include an organic solvent, such as an aromatic solvent, a halogenated hydrocarbon solvent, an alcohol solvent, or a combination thereof. The solution can further include a buffering agent, such as a carbonate salt. For example, the silyl protected diamine compound in a toluene solvent can be added slowly to a cooled solution including toluene and acryloyl chloride. When mixing, the solution can be maintained at a temperature in a range of −2° C. to 20° C., such as in a range of −2° C. to 5° C. The protected diacrylamide compound or analog can be extracted using an aqueous solution, precipitated using methanol, and filtered. In an example, the reaction mixture, extract, precipitate and filtrate are maintained at a temperature below 40° C., such as below 35° C., throughout the process. The filtrate can be further purified using chromatography.

In an alternative example, the silyl protected diamine compound in aqueous-organic two-phase systems can be mixed with an activated acrylate, such as acryloyl chloride or acryloyl anhydride, to form a protected diacrylamide compound or analog thereof. The organic phase can include an organic solvent such as an aromatic solvent, a halogenated hydrocarbon solvent, an alcohol solvent or a combination thereof. The aqueous phase can include a buffering agent, such as a carbonate salt. For example, acryloyl chloride can be added slowly to a cooled two-phase system comprised of a dichloromethane solution of the protected diamine compound and an aqueous solution of $K_2CO_3$. When mixing, the two-phase system can be maintained at a temperature in a range of −2° C. to 20° C., such as in a range of −2° C. to 5° C. The organic phase containing the protected diacrylamide compound or dialkylacrylamide analog can be separated from an aqueous phase, washed with water, brine and purified using chromatography.

In an alternative example, a hydroxylated diamine compound including one or more hydroxyl groups can be mixed with an activated acrylate, such as acryloyl chloride or acryloyl anhydride, or alkylacrylate analog to form a diacrylamide compound or analog. An exemplary hydroxylated diamine includes alkyl-diyl bis hydroxyalkyl acrylamide, hydroxyalkyl diyl-diacrylamide, bishydroxyalkyl-diyl diacrylamide, a derivative thereof, an analog thereof, or a combination thereof. The solution can include an organic solvent, such as an aromatic solvent, a halogenated hydrocarbon solvent, an alcohol solvent, or a combination thereof. The solution can further include a buffering agent, such as a carbonate salt. For example, a solution including the diamine compound, toluene, and optionally methanol can be added to acryloyl chloride or acryloyl anhydride dissolved in toluene. When mixing, the solution can be maintained at a temperature in a range of −2° C. to 20° C., such as in a range of −2° C. to 5° C. The diacrylamide compound can be extracted using a buffered aqueous solution, precipitated, and filtered. The diacrylamide compound can be further purified using dry flash chromatography.

The diacrylamide compound can be re-dissolved and reacted with a silylation reagent, such as silyl chloride, silyl triflate, or silazane, in a solvent to form a protected diacrylamide. For example, the silyl chloride can be tert-butyldimethylsilyl chloride, trimethylsilyl chloride, triethylsilyl chloride, diphenyl methyl silyl chloride, chlorotriphenylsilane or a combination thereof. In an example, the silyl trifluoromethanesulfonates ("triflate") include tert-butyldimethylsilyl trifluoromethanesulfonate, trimethylsilyl trifluoromethanesulfonate, triethylsilyl trifluoromethanesulfonate, or a combination thereof. An example of a silazane is diphenylmethyl(dimethylamino)silane. The solvent can include a DMF solvent. In addition, the mixture can include imidazole or a derivative thereof. The reactive mixture can be stirred for at least 8 hours under an inert atmosphere. The product can be extracted and washed.

While the above examples use acryloyl chloride or acryloyl anhydride, amide forming chemistries including N-hydroxysuccinimide (NHS), dicyclohexylcarbodiimide (DCC), N,N'-diisopropylcarbodiimide (DIC), or combinations thereof can be used in place of reacting with acryloyl chloride or anhydride.

EXAMPLES

Example 1 t-Butyldimethylsilylchloride (25.23 g, 167 mmol) is added to a mixture of ethylene diaminoethanol (12.01 g, 81.0 mmol)

and imidazole (11.34 g, 166 mmol) in DMF (112 mL), in four portions over a period of 50 minutes of which the mixture was cooled in an ice bath the last 25 minutes. The reaction mixture is diluted with DMF (50 mL) and stirred over night at room temperature. It is then quenched with water (155 mL), extracted with diethyl ether (approx. 200 mL), and washed with water (approx. 200 mL) and brine (approx. 200 mL), which leads to a crystalline precipitate. The organic phase is then dried over MgSO4 and evaporated, giving 18.09 g product, yellow oil. The pH in the aqueous phase containing precipitate is increased to pH 8-8.5 with 5% NaHCO3. This aqueous phase is then extracted with diethyl ether and dried over MgSO4. Evaporation gives a further 3.80 g product.

$K_2CO_3$ (6.32 g, 45.9 mmol) is added to a solution of acryloyl chloride (3.11 g, 35.2 mmol) in toluene (30 mL). The mixture is cooled in an ice bath. A solution of N,N'-bis(2-(t-butyl dimethylsilyloxy)ethyl)ethane-1,2-diamine (3.80 g, 10.1 mmol) in toluene (80 mL) is added drop wise over a period of 15 minutes. The reaction mixture is allowed to gradually reach room temperature and is stirred over night for approximately 20 h under an inert atmosphere.

The reaction mixture is cooled in an ice bath, and cold water (150 mL) is added. The product is extracted with diethyl ether and washed with 5% $NaHCO_3$ and water. The ether phase is dried ($MgSO_4$). Before evaporation, MEHQ (1.2 mg) is added to the ether phase, and the temperature of the water bath is kept below 30° C. The crude product is purified by $SiO_2$ column with hexane:EtOAc (8:2 to 1:1). Before evaporation of the fractions, MEHQ (1.5 mg) is added. The temperature of the water bath is kept below 30° C., providing 2.80 g.

Example 2

Acryloyl chloride (38 mL, 0.47 mol) is dissolved in 500 mL toluene at 0° C. before potassium carbonate (89.83 g, 0.65 mol) is added. 1,3-Diamino-2-propanol (11.72 g, 0.13 mol) is dissolved in 250 mL toluene and 50 mL methanol is added drop wise over 30 minutes at 0° C. The reaction mixture is stirred for 2 hours at 0° C. before it is poured into 500 mL water while stirring. An amount of 500 mL 0.1M HCl is added followed by 500 mL 0.1M NaOH. The layers are separated and the aqueous phase is reduced to ~0.4 L using a rotary evaporator, keeping the temperature in the water bath under 35° C. An amount of 500 mL methanol is added, leading to precipitation. The precipitate is removed by filtration and the filter cake is washed with 500 mL methanol. The combined filtrate is reduced using a rotary evaporator, keeping the temperature in the water bath under 35° C. The crude product is re-dissolved in 50 mL methanol, 25 g $SiO_2$ is added, and the mixture is reduced using a rotary evaporator, keeping the temperature in the water bath under 35° C.

The product mixture is purified using dry flash chromatography on $SiO_2$ with a column diameter of 6.5 cm and column height of 9 cm. The eluent is dichloromethane using a gradient of methanol from 0 to 12.5% to provide a yield of 12.90 g, 65.1 mmol, 50%.

Example 3

An N,N'-(2-hydroxypropane-1,3-diyl)diacrylamide is formed prior to adding protection groups.

To a solution of acryloyl chloride (34 ml, 0.42 mol) in dry acetonitrile (250 ml) is added potassium carbonate (83.4 g, 0.60 mol), followed by slow addition of a solution 1 of 1,3-diamino-2-propanol (10.6 g, 0.12 mol) in dry acetonitrile (450 ml) with stirring at 0° C. After one hour, MeOH (140 ml) is added and the reaction mixture concentrated to a small volume. The white suspension is transferred to a column loaded with silica gel and the product is isolated by dry flash chromatography (DCM:MeOH 95:5-80:20 gradient) to afford 10.75 gram (45%) of the title compound as a colorless solid. Sonication and gentle heating are used for dissolution.

Example 4

A solution of $K_2CO_3$ (61.6 g, 446 mmol) in 170 mL of water is added into a solution of $N^1,N^2$-bis2-(t-butyldimethylsilyloxy)ethyl)ethane-1,2-diamine (37.3 g, 99.1 mmol) in 220 mL of dichloromethane while stirring vigorously at an ice bath temperature. Acryloyl chloride (24.2 mL, 298 mmol) is added into the above biphasic mixture dropwise over a period of 10 min while stirring vigorously at an ice-water bath temperature. After addition is complete, the solution is stirred an additional 15 min.

The above reaction mixture is transferred to a separating funnel which contains 100 mL of dichloromethane. The separated organic layer is washed with water (2×300 mL) and brine (300 mL). The collected organic layer is filtered through a Biotage phase separator (150 mL) and is concentrated under vacuum using bath temperature below 20° C. The resulting crude product is purified by Biotage SNAP 340 column elution with first 10% ethyl acetate in hexane followed by 10-50% ethyl acetate in hexane. To the combined desired fractions is added about 9 mg of MEHQ before evaporation. The temperature of the water bath is kept below 30° C., providing a pure desired product, 30.5 g (63% yield).

Example 5

A silyl protected acrylamide monomer, (N-(2-((tert-butyldimethylsilyl)oxy)ethyl)acrylamide) (tBDMS-HEAM), is polymerized with a N,N'-(ethane-1,2-diyl)bis(N-((tert-butyldimethylsilyl)oxy)ethyl)acrylamide (tBDMS EBHEAM) crosslinker in a dispersed phase formed from polystyrene particles and is deprotected to form a hydrogel particle.

A concentrated PVA solution is formed from 80 g polyvinylalcohol (PVA) slowly added to 2000 g water, followed by stirring and heating to 80° C. for 1 hour and cooling.

To 88 g of the concentrated PVA solution, 785 g water, 0.88 g SDS, and 3.33 g borax are added to from a PVA borax solution.

A monomer emulsion is formed from 7.82 g toluene, 0.040 g 2,2'-azobis-(2-methylbutyronitrile) (AMBN), 2.06 g tBDMS HEAM, 0.51 g tBDMS-EBHEAM (95 purity) and 92.9 g PVA borax solution mixed by ultraturax for 2 minutes, and further homogenized for 5 minutes.

In a 0.5 L reactor, 1.65 g of a water dispersion of seed particles (seed diameter 0.319 μm, 8.07 weight % solids) is mixed with 88.34 g of the monomer emulsion. Argon gas (10-20 ml/min) is bubbled through the mixture while stirring and heating 1 hour at 30° C. and 2 hours at 40° C. The argon flow is stopped, and heating and stirring continued for 3 hours at 80° C.

The reaction mixture is transferred to a 1 liter centrifugation flask and centrifuged in a Sorvall RC3CPlus centrifuge for 50 minutes at 4500 RPM. The creamy flotation product is collected and is centrifuged twice in THF.

To 83.9 g of the THF swollen gel sediment, the same weight of glacial acetic acid and half the weight of water is added. The mixture is shaken at room temperature overnight. The gel is worked by removing the supernatant after centrifugation and adding THF and water in a ratio of THF:water 1:1 two times and water once, followed by three times with DMF.

The solids content of the dispersion is determined to be 1.63 g. The diameter of a water swollen gel can be measured in a microscope with phase contrast equipment and is on average 1.6 μm. The CV is not greater than 5.0%.

Example 6

A silyl protected acrylamide monomer, (N-(2-((tert-butyldimethylsilyl)oxy)ethyl)acrylamide) (tBDMS-HEAM), is polymerized with a tBDMS-EBHEAM crosslinker in a dispersed phase formed from polystyrene particles and is deprotected to form a hydrogel particle.

A concentrated PVA solution is formed from 80 g polyvinylalcohol (PVA) slowly added to 2000 g water, followed by stirring and heating to 80° C. for 1 hour and cooling.

To 88 g of the concentrated PVA solution, 785 g water, 0.88 g SDS, and 3.33 g borax is added to form a PVA borax solution.

A monomer emulsion is formed from 7.82 g toluene, 0.040 g 2,2'-azobis-(2-methylbutyronitrile) (AMBN), 2.06 g tBDMS HEAM, 0.96 g tBDMS-EBHEAM (95 purity) and 92.9 g PVA borax solution mixed by ultraturax for 2 minutes, and further homogenized for 5 minutes.

In a 0.5 L reactor, 1.65 g of a water dispersion of seed particles (seed diameter 0.319 μm, 8.07 weight % solids) is mixed with 88.34 g of the monomer emulsion. Argon gas (10-20 ml/min) is bubbled through the mixture while stirring and heating 1 hour at 30° C. and 2 hours at 40° C. The argon flow is stopped, and heating and stirring continued for 3 hours at 80° C.

The reaction mixture is transferred to a 1 liter centrifugation flask and centrifuged in a Sorvall RC3CPlus centrifuge for 50 minutes at 4500 RPM. The creamy flotation product is collected and is centrifuged twice in THF.

To 83.9 g of the THF swollen gel sediment, the same weight of glacial acetic acid and half the weight of water is added. The mixture is shaken at room temperature over night. The gel is worked by removing the supernatant after centrifugation and adding THF and water in a ratio of THF:water 1:1 two times and water once, followed by three times with DMF.

The solids content of the dispersion is determined to be 1.63 g. The diameter of a water swollen gel can be measured in a microscope with phase contrast equipment and is on average 1.6 μm. The CV is not greater than 5.0%.

Example 7

A silyl protected acrylamide monomer, (N-(2-((tert-butyldimethylsilyl)oxy)ethyl)acrylamide) (tBDMS-HEAM), is polymerized with N,N'-(ethane-1,2-diyl)bis(N-((tert-butyldimethylsilyl)oxy)ethyl)acrylamide) (TBDMS EBHEAM) as crosslinker in a dispersed phase formed from polystyrene particles and is deprotected to form a hydrophilic particle.

A concentrated PVA solution is prepared by adding 80 g polyvinylalcohol (PVA) slowly to 2000 g water while stirring. The mixture is stirred and is heated to 80° C. for 1 hour and cooled.

To 241.8 g of the concentrated PVA solution, 2129.6 g water, 2.32 g SDS and 9.97 g borax are added to form a PVA borax solution.

A monomer emulsion is prepared by mixing 72.68 g toluene, 0.29 g 2,2'-azobis-(2-methylbutyronitrile) (AMBN), 14.59 g tBDMS HEAM, 4.46 g TBDMS EBHEAM and 835.8 g PVA borax solution, mixed by ultraturax for 2 minutes, and further homogenized for 9 minutes in a high pressure Gauline APV-100 homogenizer at 400 Bar.

In a 1 L reactor, 16.86 g of a water dispersion of seed particles (seed diameter 0.319 μm, 8.07 weight % solids) is mixed with 897 g of the monomer emulsion. The mixture is stirred and heated for 3 hour at 40° C. while bubbling argon through the mixture at 0.05 l/min for the first 2 hours and at 0.15 L/min for 1 hour. The argon flow is then stopped and the emulsion is heated for 3 hours at 80° C.

The reaction mixture is transferred to a 1 liter centrifugation flask and centrifuged in a Sorvall RC3CPlus centrifuge for 60 minutes at 4700 RPM. The creamy flotation product is transferred to a new 500 mL glass flask and resuspended to 370.74 g with water, the pH is adjusted to 3.86 with 21.09 g 0.5 M acetic acid. The mixture is stirred at 60° C. for 2 hours.

The gel is worked up by adding 9 volumes of THF to the deprotected gel, and centrifuged in a Sorvall RC3CPlus centrifuge for 10 minutes at 3500 RPM, followed by two centrifugations with DMF and two centrifugations with dry DMF, all with addition of 7.5% THF prior to centrifugation. The solids content of the gel in DMF is determined to be 6.37 g. The bead dispersion is transferred to water and inspected by microscopy and the bead diameter is 1.7 micron in water.

Example 8

A silyl protected acrylamide monomer, (N-(2-((tert-butyldimethylsilyl)oxy)ethyl)acrylamide) (tBDMS-HEAM), is polymerized with a tBDMS-EBHEAM crosslinker in a dispersed phase formed from polystyrene particles and is deprotected to form a hydrogel particle.

An emulsion is prepared by first dissolving 1.74 g SDS in 290.00 g water and then adding 14.50 g acetone and 29.00 g bis(2-ethylhexyl) adipate (DOA). The emulsion is mixed by ultraturax for 2 minutes, and further homogenized for 5.6 minutes in a high pressure Gauline APV-100 homogenizer at 400 Bar.

31.14 g of this emulsion is added to 43.89 g of seed particles (seed diameter 0.140 μm, 4.85 weight % solids) in a flask. The mixture is shaken at 40° C. for 40 h in a shaking bath for activation.

An SDS borax solution is prepared by dissolving 4.54 g SDS and 9.69 g borax to 2369.8 g water.

A monomer emulsion is formed from 125.29 g 2-phenethyl acetate, 0.468 g 2,2'-azobis-(2-methylbutyronitrile) (AMBN), 19.51 g tBDMS HEAM, 5.99 g tBDMS-EBHEAM and 816.75 g SDS borax solution mixed by ultraturax for 5 minutes, and further homogenized for 9.68 minutes.

In a 1 L reactor, 62.53 g of a water dispersion of activated seed particles is mixed with 938.1 g of the monomer emulsion. The mixture is stirred and heated at 40° C. for 2 h. The mixture is further stirred and heated at 40° C. for another hour while argon gas (150-200 ml/min) is bubbled through the mixture. The amount of $O_2$ in the emulsion at this point is measure to be 0 ppb. The argon flow is stopped, and heating and stirring continued for 10 hours at 70° C.

The reaction mixture is transferred to four 250 mL centrifugation flasks and centrifuged in a Beckman Coulter Avanti J-20 XP centrifuge for 60 minutes at 13000 RPM. The supernatants are discarded and the sediments are collected and transferred into a glass flask by adding water.

pH of the aqueous dispersion of gels is adjusted to 3.8 by adding 0.5 M acetic acid solution. The acidified gel dispersion is shaken at 60° C. in a shaking bath for 2 h and cooled.

The gel dispersion is transferred into three 1 L flasks, 300 g THF is added to each, the flasks are shaken at room temperature for 30 min on a shaking table and centrifuged in a Thermo Scientific Thermo Scientific Sorvall RC3CPlus centrifuge for 25 minutes at 4500 RPM. The upper phases of resulting biphasic mixtures are discarded, 50 g THF is added to each flask, the flasks are shaken at room temperature for 30 min on a shaking table and centrifuged for 25 minutes at 4500 RPM. Supernatants are discarded.

Contents of each flask are divided into two 250 mL centrifuge flasks. Approximately 100 g DMF is added on each flask and the flasks are shaken overnight at room temperature on a shaking table. Contents of each flask are totaled to 200 g by adding 20 g THF and necessary amount of DMF. The flasks are centrifuged in a Beckman Coulter Avanti J-20 XP centrifuge for 70 minutes at 13000 RPM. Supernatants are discarded.

Approximately 100 g DMF is added on each flask and the flasks are shaken for 40 min at room temperature on a shaking table. Contents of each flask are totaled to 200 g by adding 20 g THF and necessary amount of DMF. The flasks are centrifuged in a Beckman Coulter Avanti J-20 XP centrifuge for 70 minutes at 13000 RPM. Supernatants are discarded and all the sediments are combined into a new flask by using minimal amounts of DMF.

The solids content of the dispersion is determined to be 2.34 g. The diameter of a water swollen gel is measured in a microscope with phase contrast equipment and is on average 0.80 µm.

Water swollen gel is further analyzed in a disc centrifuge instrument (CPS Instruments, Inc, model DC20000) using a gradient of 3 and 7 w % sucrose solutions and a rotation speed of 15000 RPM. The diameter is measured as 0.4995 µm using a particle density of 1,032 g/ml. CV (number) is measured as 3.6%.

Example 9

A silyl protected acrylamide monomer, (N-(2-((tert-butyldimethylsilyl)oxy)ethyl)acrylamide) (tBDMS-HEAM), is polymerized with a tBDMS-EBHEAM crosslinker in a dispersed phase formed from polystyrene particles and is deprotected to form a hydrogel particle.

An emulsion is prepared by first dissolving 1.98 g SDS in 330.05 g water and then adding 16.51 g acetone and 33.00 g DOA. The emulsion is mixed by ultraturax for 2 minutes, and further homogenized for 6.4 minutes in a high pressure Gauline APV-100 homogenizer at 400 Bar.

37.71 g of this emulsion is added to 68.57 g of seed particles (seed diameter 0.081 µm, 4.91 weight % solids) in a flask. The mixture is shaken at 40° C. for 20 h in a shaking bath for activation.

An SDS borax solution is prepared by dissolving 3.77 g SDS and 7.59 g borax to 1975.6 g water.

A monomer emulsion is formed from 33.89 g 2-phenethyl acetate, 0.126 g 2,2'-azobis-(2-methylbutyronitrile) (AMBN), 5.26 g tBDMS HEAM, 1.61 g tBDMS-EBHEAM and 223.32 g SDS borax solution mixed by ultraturax for 5 minutes, and further homogenized for 2.6 minutes.

In a 250 mL reactor, 20.31 g of a water dispersion of activated seed particles is mixed with 228.23 g of the monomer emulsion. The mixture is stirred and heated at 40° C. for 2 h. The mixture is further stirred and heated at 40° C. for another hour while argon gas (150-200 ml/min) is bubbled through the mixture. The amount of $O_2$ in the emulsion at this point is measure to be 230 ppb. The argon flow is stopped, and heating and stirring continued for 10 hours at 70° C.

The reaction mixture is transferred to a 250 mL centrifugation flask and centrifuged in a Beckman Coulter Avanti J-20 XP centrifuge for 90 minutes at 12500 RPM. The supernatant is discarded and the sediment is collected and transferred into a glass flask by adding water.

pH of the aqueous dispersion of gels is adjusted to 3.85 by adding 0.5 M acetic acid solution. The acidified gel dispersion is shaken at 60° C. in a shaking bath for 2.5 h and cooled.

The gel dispersion is transferred into a 1 L flask, 170.06 g THF is added, the flask is shaken at room temperature for 10 min on a shaking table and centrifuged in a Thermo Scientific Thermo Scientific Sorvall RC3CPlus centrifuge for 30 minutes at 4500 RPM. The upper phase of resulting biphasic mixture is discarded. 86.81 g THF is added, the flask is shaken at room temperature for 15 min on a shaking table and centrifuged for 30 minutes at 4500 RPM. Supernatant is discarded.

200 g DMF is added on the gel sediment in 1 L flask and this suspension is divided in two 250 mL centrifuge flasks. The flasks are shaken at room temperature for 153 min on a shaking table and contents of each flask are totaled to 200 g by adding 30 g THF and necessary amount of DMF. The flasks are centrifuged in a Beckman Coulter Avanti J-20 XP centrifuge for 90 minutes at 14000 RPM. Supernatants are discarded.

100 g DMF is added to each flask and the suspensions are shaken at room temperature for 20 min on a shaking table. Contents of each flask are totaled to 200 g by adding 30 g THF and necessary amount of DMF and the flasks are centrifuged in a Beckman Coulter Avanti J-20 XP centrifuge for 90 minutes at 14000 RPM. Supernatants are discarded and all the sediments are combined into a new flask by using minimal amounts of DMF. The solids content of the dispersion is determined to be 2.03 g.

Water swollen gel is further analyzed in a disc centrifuge instrument (CPS Instruments, Inc, model DC20000) using a gradient of 3 and 7 w % sucrose solutions and a rotation speed of 20000 RPM. The diameter is measured as 0.2885 µm using a particle density of 1.032 g/ml. CV (number) is measured as 5.56%.

Particular embodiments of the above-described protective diacrylamide compound exhibit particular technical advantages over other crosslinkers. For example, such protected diacrylamide compounds can be utilized during polymerization reactions in hydrophobic solvents. In the context of an emulsion, such protected diacrylamide compounds preferentially reside within hydrophobic phase, whether the dispersed phase or the continuous phase. Diacrylamide compounds protected with silyl protection groups including at least one ethyl, propyl, or butyl functionality provide advantageous preference for hydrophobic phases. In another example, diacrylamide compounds protected with silyl protection groups including at least one branched alkyl functionality provide advantageous preference for hydrophobic phases. In particular, diacrylamide compounds having a log(p) value within a desirable range advantageously reside in a hydrophobic phase and are particularly useful in emulsion polymerization. When the resulting polymer is desirably hydrophilic, it is preferred that the diacrylamide analogous compound have a log(p) value within a desirable range.

In a first aspect, a compound has formula I above or an analog thereof, wherein R1 and R2 are independently selected from alkyl, heteroalkyl, cycloalkyl, hydroxyalkyl, acyl, aryl, ether derivatives thereof, or a combination thereof, and R3, R4, R5, R6, and R7 are independently selected from alkyl, heteroalkyl, cycloalkyl, hydroxyalkyl, acyl, oxycarbonyl, aryl, ether derivatives thereof, a silyl, or a combination thereof.

In an example of the first aspect, R1 or R2 is a C1-C6 alkyl. For example, R1 or R2 is a methyl or ethyl group.

In another example of the first aspect and the above examples, at least one of R3, R4, R5, R6, and R7 is an aryl group. For example, the aryl group can be phenyl, tolyl, xylyl, or poly-aryl, or an ether derivative thereof. In particular, the aryl group can be tolyl.

In a further example of the first aspect and the above examples, at least one of R3, R4, R5, R6, and R7 is alkyl, or an ether derivative thereof. The alkyl can be a C1-C6 alkyl or an ether derivative thereof. For example, the alkyl group can be a methyl, ethyl, propyl, butyl, ether derivative thereof, or combination thereof, such as ethyl, propyl, butyl, ether derivative thereof, or combination thereof. In particular, the alkyl can be butyl and the butyl is tert-butyl.

In an additional example of the first aspect and the above examples, R6 or R7 is hydrogen.

In another example of the first aspect and the above examples, the log(p) of the compound is greater than 1.0, at least 1.2, at least 1.3, at least 1.50, at least 1.7, or at least 2.0. The log(p) of the compound may be not greater than 10.0, such as not greater than 5.0. Further, the log(p) of a deprotected analogous compound is not greater than 0.5 not greater than 0.3, not greater than 0.2, not greater than 0.1, not greater than 0, not greater than −0.5, or not greater than −1.0. The log(p) of a deprotected analogous compound is at least −10.0, such as at least −5.0.

In a second aspect, a compound has the formula II above or an analog thereof, wherein R1 or R2 are independently selected from alkyl, heteroalkyl, cycloalkyl, hydroxyalkyl, acyl, aryl, ether derivatives thereof, or a combination thereof, and R3, R4, or R5 are independently selected from alkyl, heteroalkyl, cycloalkyl, hydroxyalkyl, acyl, aryl, ether derivatives thereof, or a combination thereof.

In an example of the second aspect, R1 or R2 is a C1-C6 alkyl, or an ether derivative thereof. For example, R1 or R2 is a methyl or ethyl group.

In another example of the second aspect and the above example, at least one of R3, R4, R5, is aryl or an ether derivative thereof. The aryl group can be phenyl, tolyl, xylyl, or poly-aryl, or an ether derivative thereof. For example, the aryl group can be tolyl.

In a further example of the second aspect and the above examples, at least one of R3, R4, or R5 is alkyl or an ether derivative thereof. For example, the alkyl is a C1-C6 alkyl or an ether derivative thereof. In particular, the alkyl group can be a methyl, ethyl, propyl, butyl, ether derivative thereof, or a combination thereof, such as an ethyl, propyl, butyl, ether derivative thereof, or a combination thereof. For example, the alkyl is butyl and the butyl is tert-butyl.

In an additional example of the second aspect and the above examples, the log(p) of the compound is greater than 1.0, at least 1.2, at least 1.3, at least 1.5, at least 1.7, or at least 2.0. The log(p) of the compound can be not greater than 10.0, such as not greater than 5.0. Further, the log(p) of a deprotected analogous compound is not greater than 0.5, not greater than 0.3, not greater than 0.2, not greater than 0.1, not greater than 0, not greater than −0.5, or not greater than −1.0. The log(p) of the deprotected analogous compound can be at least −10.0, such as at least −5.0.

In a third aspect, a compound has the formula III above or an analog thereof, R1, R2, or R3 are independently selected from alkyl, heteroalkyl, cycloalkyl, hydroxyalkyl, acyl, aryl, ether derivatives thereof, or a combination thereof.

In an example of the third aspect, at least one of R1, R2 or R3 is aryl or an ether derivative thereof. For example, the aryl group can be phenyl, tolyl, xylyl, or poly-aryl, or an ether derivative thereof.

In another example of the third aspect or the above example, at least one of R1, R2 or R3 is an alkyl group or an ether derivative thereof. For example, the alkyl group can be a methyl, ethyl, propyl, or butyl, an ether derivative thereof, or a combination thereof, such as an ethyl, propyl, butyl, ether derivative thereof, or a combination thereof. In an example, the alkyl group is methyl or ethyl. In an additional example, the alkyl group is tert-butyl.

In a further example of the third aspect or the above examples, the log(p) of the compound is greater than 1.0, at least 1.2, at least 1.3, at least 1.5, at least 1.7, or at least 2.0. The log(p) of the compound is not greater than 10.0, such as not greater than 5.0. Further, the log(p) of a deprotected analogous compound is not greater than 0.5, not greater than 0.3, not greater than 0.2, not greater than 0.1, not greater than 0, not greater than −0.5, or not greater than −1.0. The log(p) of the deprotected analogous compound is at least −10.0, such as at least −5.0.

In a fourth aspect, a compound has the formula XII above or an analog thereof or monosilylated derivative thereof, wherein R4, R5, or R6 are independently selected from alkyl, heteroalkyl, cycloalkyl, hydroxyalkyl, acyl, aryl, ether derivatives thereof, or a combination thereof, and R1, R2, R3, R7, R8, or R9 are independently selected from alkyl, heteroalkyl, cycloalkyl, hydroxyalkyl, acyl, aryl, ether derivatives thereof, or a combination thereof.

In an example of the fourth aspect, R4, R5 or R6 is a C1-C6 alkyl or an ether derivative thereof. For example, R4, R5 or R6 is methyl or ethyl.

In another example of the fourth aspect or the above example, at least one of R1, R2, R3, R7, R8, or R9 is aryl or an ether derivative thereof. For example, the aryl group is phenyl, tolyl, xylyl, or poly-aryl, or an ether derivative thereof.

In an additional example of the fourth aspect or the above examples, at least one of R1, R2, R3, R7, R8, or R9 is alkyl or an ether derivative thereof. For example, the alkyl can be a methyl, ethyl, propyl, or butyl, or an ether derivative thereof. The alkyl can be methyl or ethyl. In another example, the alkyl is tert-butyl.

In a further example of the fourth aspect or the above examples, the log(p) of the compound is greater than 2.0, at least 2.2, at least 2.3, at least 2.5, at least 2.7, or at least 3.0. The log(p) of the compound is not greater than 10.0, such as not greater than 5.0. Further, the log(p) of a deprotected analogous compound is not greater than 0.5, not greater than 0.3, not greater than 0.2, not greater than 0.1, not greater than 0, not greater than −0.5, or not greater than −1.0. The log(p) of the deprotected analogous compound is at least −10.0, such as at least −5.0.

In a fifth aspect, a compound has the formula XIII above or an analog thereof or monosilylated derivative thereof, wherein R4 or R5 are independently selected from alkyl, heteroalkyl, cycloalkyl, hydroxyalkyl, acyl, aryl, ether derivatives thereof, or a combination thereof, and R1, R2, R3, R6, R7, or R8 are independently selected from alkyl, heteroalkyl, cycloalkyl, hydroxyalkyl, acyl, aryl, ether derivatives thereof, or a combination thereof.

In an example of the fifth aspect, R4 or R5 is methyl or ethyl.

In another example of the fifth aspect and the above example, at least one of R1, R2, R3, R6, R7, or R8 is aryl or an ether derivative thereof.

In an additional example of the fifth aspect or the above examples, the aryl group is phenyl, tolyl, xylyl, or poly-aryl, or an ether derivative thereof. For example, the aryl group can be tolyl.

In a further example of the fifth aspect or the above examples, at least one of R1, R2, R3, R6, R7, or R8 is alkyl or an ether derivative thereof. For example, the alkyl group can be be a methyl, ethyl, propyl, or butyl or an ether derivative thereof, such as an ethyl, propyl, or butyl or an ether derivative thereof. The alkyl group can be methyl or ethyl. In another example, the alkyl group can be tert-butyl group.

In another example of the fifth aspect or the above examples, the log(p) of the compound is greater than 2.0, at least 2.2, at least 2.3, at least 2.5, at least 2.7, or at least 3.0. The log(p) of the compound is not greater than 10.0, such as not greater than 5.0. Further, the log(p) of a deprotected analogous compound is not greater than 0.5, not greater than 0.3, not greater than 0.2, not greater than 0.1, not greater than 0, not greater than −0.5, or not greater than −1.0. The log(p) of the deprotected analogous compound is at least −10.0, such as at least −5.0.

In a sixth aspect, a compound has the formula VII above or an analog thereof or monosilylated derivative thereof, wherein R1 or R2 are independently selected from alkyl, heteroalkyl, cycloalkyl, hydroxyalkyl, acyl, aryl, ether derivatives thereof, or a combination thereof or represent a direct bond between a nitrogen and a hydroxylated carbon, and R3, R4, R5, R6, R7, R8, R9, or R10 are independently selected from hydrogen, alkyl, heteroalkyl, cycloalkyl, hydroxyalkyl, acyl, oxycarbonyl, aryl, ether derivatives thereof, silyl, or a combination thereof.

In an example of the sixth aspect, at least one of R1 or R2 is alkyl. For example, at least one of R1 or R2 can be methyl or ethyl.

In another example of the sixth aspect or the above examples, at least one of R3, R4, R5, R6, R7, R8, R9, or R10 is aryl or an ether derivative thereof. For example, at least one of R3, R4, R5, R6, R7, R8, R9, or R10 can be phenyl, tolyl, xylyl, or poly-aryl, or an ether derivative thereof.

In a further example of the sixth aspect or the above examples, at least one of R3, R4, R5, R6, R7, R8, R9, or R10 can be alkyl or an ether derivative thereof. For example, at least one of R3, R4, R5, R6, R7, R8, R9, or R10 can be methyl, ethyl, propyl, or butyl, an ether derivative thereof, or a combination thereof. In an example, at least one of R3, R4, R5, R6, R7, R8, R9, or R10 is a methyl or ethyl group. In another example, at least one of R3, R4, R5, R6, R7, R8, R9, or R10 is tert-butyl.

In an additional example of the sixth aspect or the above examples, R6 or R7 is hydrogen. In an alternative example of the sixth aspect or the above examples, R6 or R7 are a C1-C6 alkyl or ether derivative thereof.

In another example of the sixth aspect or the above examples, the log(p) of the compound is greater than 2.5, at least 2.7, at least 2.8, at least 3.0, at least 3.2, or at least 3.5. Further, the log(p) of a deprotected analogous compound is not greater than 0.5, not greater than 0.3, not greater than 0.2, not greater than 0.1, not greater than 0, not greater than −0.5, or not greater than −1.0.

In a seventh aspect, a method of forming a compound includes mixing an activated acrylate and a hydroxylated diamine compound to form a hydroxylated diacrylamide compound, separating the hydroxylated diacrylamide compound, and mixing a silylation reagent, such as silyl chloride, silyl triflate, or silazane, with the hydroxylated diacrylamide compound under reactive conditions to form a silyl protected diacrylamide compound.

In an example of the seventh aspect, the activated acrylate is acryloyl chloride, acryloyl anhydride, an alkylacryloyl analog thereof, or a combination thereof.

In another example of the seventh aspect and the above example, mixing the activate acrylate and the hydroxylated diamine compound includes mixing in an organic solvent. For example, the organic solvent includes an aromatic solvent, a halogenated hydrocarbon solvent, an alcohol solvent, or a combination thereof.

In a further example of the seventh aspect and the above examples, mixing the activated acrylate and the hydroxylated diamine compound includes mixing at a temperature in a range of −2° C. to 20° C. For example, the temperature can be in a range of −2° C. to 5° C.

In an additional example of the seventh aspect and the above examples, separating includes precipitating the hydroxylated diacrylamide compound and filtering the precipitate.

In another example of the seventh aspect and the above examples, the silyl chloride is tert-butyldimethylsilyl chloride, trimethylsilyl chloride, triethylsilyl chloride, diphenyl methyl silyl chloride, chlorotriphenylsilane or a combination thereof. In an example of the seventh aspect and the above examples, the silyl trifluoromethanesulfonates ("triflate") includes tert-butyldimethylsilyl trifluoromethanesulfonate, trimethylsilyl trifluoromethanesulfonate, triethylsilyl trifluoromethanesulfonate, or a combination thereof. An example of a silazane includes diphenylmethyl(dimethylamino)silane.

In a further example of the seventh aspect and the above examples, the hydroxylated diacrylamide is alkyl-diyl bis hydroxyalkyl acrylamide, hydroxyalkyl diyl-diacrylamide, bishydroxyalkyl-diyl diacrylamide, a derivative thereof, or a combination thereof.

In an eighth aspect, a method of forming a compound includes mixing a silylation reagent, such as silyl chloride, silyl triflate, or silazane, with a hydroxylated diacrylamide under reactive conditions to form silyl protected diacrylamide in a solution and separating the silyl protected diacrylamide from the solution.

In an example of the eighth aspect, the silyl chloride is tert-butyldimethylsilyl chloride, trimethylsilyl chloride, triethylsilyl chloride, diphenyl methyl silyl chloride, chlorotriphenylsilane or a combination thereof. In an example of the eighth aspect and the above examples, the silyl trifluoromethanesulfonates ("triflate") includes tert-butyldimethylsilyl trifluoromethanesulfonate, trimethylsilyl trifluoromethanesulfonate, triethylsilyl trifluoromethanesulfonate, or a combination thereof. An example of a silazane includes diphenylmethyl(dimethylamino)silane.

In a ninth aspect, a method of forming a compound includes mixing a silylation reagent, such as silyl chloride, silyl triflate, or silazane, with a hydroxylated diamine compound under first reactive conditions to form a product in a first solution, separating the product from the first solution, and mixing the product with an activated acrylate under second reactive conditions in a second solution to form a silyl protected diacrylamide compound.

In an example of the ninth aspect, the activated acrylate is acryloyl chloride, acryloyl anhydride, an alkylacryloyl analog thereof, or a combination thereof.

In another example of the ninth aspect and the above example, the silyl chloride is tert-butyldimethylsilyl chloride, trimethylsilyl chloride, triethylsilyl chloride, diphenyl methyl silyl chloride, chlorotriphenylsilane or a combination thereof. In an example of the ninth aspect and the above examples, the silyl trifluoromethanesulfonates ("triflate") includes tert-butyldimethylsilyl trifluoromethanesulfonate, trimethylsilyl trifluoromethanesulfonate, triethylsilyl trifluoromethanesulfonate, or a combination thereof. An example of a silazane includes diphenylmethyl(dimethylamino)silane.

In a further example of the ninth aspect and the above examples, the hydroxylated diamine is alkyl-diyl bis hydroxyalkyl acrylamide, hydroxyalkyl diyl-diacrylamide, bishydroxyalkyl-diyl diacrylamide, a derivative thereof, or a combination thereof.

In an additional example of the ninth aspect and the above examples, mixing the product with the activated acrylate includes mixing in an organic solvent. For example, the organic solvent includes an aromatic solvent, a halogenated hydrocarbon solvent, an alcohol solvent, or a combination thereof.

In another example of the ninth aspect and the above examples, mixing the product and the activated acrylate includes mixing at a temperature in a range of −2° C. to 20° C. For example, the temperature can be in a range of −2° C. to 5° C.

In a further example of the ninth aspect and the above examples, the first solution includes a DMF solvent. In another example of the ninth aspect and the above examples, the first solution includes imidazole or a derivative thereof. In an additional example of the ninth aspect and the above examples, the second solution includes a buffering agent. In a further example of the ninth aspect and the above examples, separating includes extracting with diethyl ether or dichloromethane.

In a tenth aspect, a method of forming a polymer includes mixing in a hydrophobic phase, a monomer and a compound of the above aspects, the monomer and the compound polymerizing to form the polymer.

In an example of the tenth aspect, the monomer is a free radical polymerizable monomer. For example, the free radical polymerizable monomer can be acrylamide, vinyl acetate, hydroxyalkylmethacrylate, or any combination thereof.

In another example of the tenth aspect and the above example, the hydrophobic phase is a dispersed phase in an emulsion.

In a further example of the tenth aspect and the above examples, the polymer includes the silyl group of the compound and wherein the method further includes removing the silyl group from the polymer.

In an eleventh aspect, a composition includes a non-aqueous solution including a diacrylamide crosslinker and a free radical polymerizable monomer. In an example of the eleventh aspect, the diacrylamide crosslinker is included in an amount relative to the free radical polymerizable monomer in a range of 0.01 wt % to 30 wt %. In a further example of the eleventh aspect and the above example, the composition further includes an aqueous phase, the non-aqueous solution dispersed within the aqueous phase as an emulsion.

Note that not all of the activities described above in the general description or the examples are required, that a portion of a specific activity may not be required, and that one or more further activities may be performed in addition to those described. Still further, the order in which activities are listed are not necessarily the order in which they are performed.

In the foregoing specification, the concepts have been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention.

As used herein, the terms "comprises," "comprising," "includes," "including," "has," "having" or any other variation thereof, are intended to cover a non-exclusive inclusion. For example, a process, method, article, or apparatus that comprises a list of features is not necessarily limited only to those features but may include other features not expressly listed or inherent to such process, method, article, or apparatus. Further, unless expressly stated to the contrary, "or" refers to an inclusive-or and not to an exclusive-or. For example, a condition A or B is satisfied by any one of the following: A is true (or present) and B is false (or not present), A is false (or not present) and B is true (or present), and both A and B are true (or present).

Also, the use of "a" or "an" are employed to describe elements and components described herein. This is done merely for convenience and to give a general sense of the scope of the invention. This description should be read to include one or at least one and the singular also includes the plural unless it is obvious that it is meant otherwise.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

After reading the specification, skilled artisans will appreciate that certain features are, for clarity, described herein in the context of separate embodiments, may also be provided in combination in a single embodiment. Conversely, various features that are, for brevity, described in the context of a single embodiment, may also be provided separately or in any subcombination. Further, references to values stated in ranges include each and every value within that range.

What is claimed is:

1. A compound of the formula:

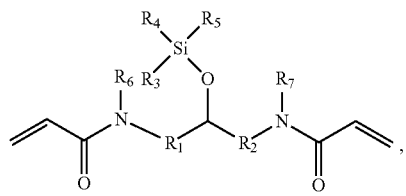

wherein R1 and R2 are independently selected from alkyl, heteroalkyl, cycloalkyl, hydroxyalkyl, acyl, aryl, ether derivatives thereof, or a combination thereof, and R3, R4, R5, R6, and R7 are independently selected from hydrogen, alkyl, heteroalkyl, cycloalkyl, hydroxyalkyl, acyl, oxycarbonyl, aryl, ether derivatives thereof, a silyl, or a combination thereof.

2. The compound of claim 1, wherein R1 or R2 is a C1-C6 alkyl.

3. The compound of claim 2, wherein R1 or R2 is a methyl or ethyl group.

4. The compound of claim 1, wherein at least one of R3, R4, R5, R6, and R7 is an aryl group.

5. The compound of claim 4, wherein the aryl group is phenyl, tolyl, xylyl, or poly-aryl, or an ether derivative thereof.

6. The compound of claim 4, wherein the aryl group is tolyl.

7. The compound of claim 1, wherein at least one of R3, R4, R5, R6, and R7 is alkyl, or an ether derivative thereof.

8. The compound of claim 7, wherein the alkyl is a C1-C6 alkyl or an ether derivative thereof.

9. The compound of claim 7, wherein the alkyl group is a methyl, ethyl, propyl, butyl, ether derivative thereof, or combination thereof.

10. The compound of claim 9, wherein the alkyl is butyl and the butyl is tert-butyl.

11. The compound of claim 1, R6 or R7 is hydrogen.

12. The compound of claim 1, wherein the log(p) of a deprotected analogous compound is not greater than 0.5 and at least −10.0.

13. The compound of claim 12, wherein the log(p) of the compound is greater than 1.0 and not greater than 10.0.

14. A compound of the formula:

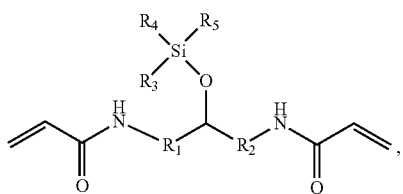

wherein R1 or R2 are independently selected from alkyl, heteroalkyl, cycloalkyl, hydroxyalkyl, acyl, aryl, ether derivatives thereof, or a combination thereof, and R3, R4, or R5 are independently selected from alkyl, heteroalkyl, cycloalkyl, hydroxyalkyl, acyl, aryl, ether derivatives thereof, or a combination thereof.

15. The compound of claim 14, wherein at least one of R3, R4, and R5 is an aryl group.

16. The compound of claim 15, wherein the aryl group is phenyl, tolyl, xylyl, or poly-aryl, or an ether derivative thereof.

17. The compound of claim 15, wherein the aryl group is tolyl.

18. The compound of claim 14, wherein at least one of R3, R4, and R5 is alkyl, or an ether derivative thereof.

19. The compound of claim 18, wherein the alkyl is a C1-C6 alkyl or an ether derivative thereof.

20. A compound of the formula:

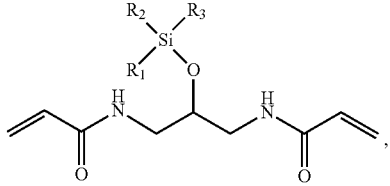

wherein R1, R2, or R3 are independently selected from alkyl, heteroalkyl, cycloalkyl, hydroxyalkyl, acyl, aryl, ether derivatives thereof, or a combination thereof.

* * * * *